(12) United States Patent
Sugimura et al.

(10) Patent No.: US 7,482,436 B2
(45) Date of Patent: Jan. 27, 2009

(54) HUMAN ANTIHUMAN INTERLEUKIN-6 ANTIBODY AND FRAGMENT OF ANTIBODY

(75) Inventors: Kazuhisa Sugimura, Kagoshima (JP); Kazuyuki Yoshizaki, Ashiya (JP); Toshihiro Nakashima, Kikuchi-gun (JP); Takumi Sasaki, Kikuchi-gun (JP)

(73) Assignee: Juridical Foundation The Chemo-Sero-Therapeutic Research Institute, Kumamoto-Ken (JP)

( * ) Notice: Subject to any disclaimer, the term of this patent is extended or adjusted under 35 U.S.C. 154(b) by 427 days.

(21) Appl. No.: 10/526,072

(22) PCT Filed: Aug. 28, 2003

(86) PCT No.: PCT/JP03/10923

§ 371 (c)(1),
(2), (4) Date: Feb. 28, 2005

(87) PCT Pub. No.: WO2004/020633

PCT Pub. Date: Mar. 11, 2004

(65) Prior Publication Data

US 2006/0240012 A1 Oct. 26, 2006

(30) Foreign Application Priority Data

Aug. 30, 2002 (JP) .............................. 2002-253036

(51) Int. Cl.
*C07K 16/24* (2006.01)
(52) U.S. Cl. ............................. 530/388.15; 530/388.23
(58) Field of Classification Search ...................... None
See application file for complete search history.

(56) References Cited

U.S. PATENT DOCUMENTS 5,959,085 A * 9/1999 Garrone et al. ........... 530/387.3
2004/0071706 A1* 4/2004 Ito et al. .................. 424/145.1

FOREIGN PATENT DOCUMENTS

WO  WO 2005/105998 A  11/2005

OTHER PUBLICATIONS

Janeway et al., Immunobiology, 5th Ed., Garland Science, pp. 94-105 (2001).*
Vajdos et al., J Mol Biol. Jul. 5, 2002;320(2):415-28.*
Rudikoff et al, Proc. Natl. Acad. Sci. USA, 79:1979-1983.*
Colman P. M.. Research in Immunology, 145:33-36, 1994.*
Chien et al., Proc Natl Acad Sci U S A. Jul. 1989;86(14):5532-6.*
Rose-John et al., J Leukoc Biol. Aug. 2006;80(2):227-36.*
Matsuda et al., J Immunol. Jan. 1, 1989;142(1):148-52.*
Chow et al., Biochemistry. Jun. 26, 2001;40(25):7593-603.*
Dictionary of Immunology, 1st edition, p. 49, 1993 (2nd edition, p. 60).
S. Akira et al; "Interleukin-6 in Biology and Medicine"; *Advances in Immunology*, vol. 54, pp. 1-78; 1993.
R. Gejima et al; "Human Single-chain FV (scFv) Antibody Specific to Human IL-6 with the Inhibitory Activity on IL-6-signaling"; *Human Antibodies*; vol. 11(4), pp. 121-129; 2002.
T. Hirano et al; "Interleukin-6: Possible Implications in Human Diseases"; *Res. Clin. Lab.*, vol. 19(1), pp. 1-10; 1989.
B. Krebs et al; "Recombinant Human Single Chain Fv Antibodies Recognizing Human Interleukin-6"; *The Journal of Biological Chemistry*; vol. 273(5), pp. 2858-2865; 1998.
J. D. Marks et al; "By-passing Immunization Human Antibodies from V-gene Libraries Displayed on Phage"; *Journal Molecular Biology*; vol. 222(3); pp. 581-597; 1991.
M. Mihara at al; "Interleukin-6 (IL-6) Induces the proliferation of Synovial Fibroblastic Cells in the Presence of Soluble IL-6 Receptor; *British Journal of Rheumatology*"; vol. 34(4); pp. 321-325; 1995.
M. Mihara et al; "Humanized Antibody to Human Interleukin-6 Receptor Inhibits the Development of Collagen Arthritis in Cynomolgus Monkeys"; *Clinical Immunology*, vol. 98(3); pp. 319-326; 2001.
S. Monier et al; "Growth Factor Activity of IL-6 in the Synovial fluid of patients with rheumatoid arthritis"; *Clinical and Experimental Rheumatology*; vol. 12(6); pp. 595-602, 1994.
F. Montero-Julian et al; "Pharmacokinetic Study of Anti-Interleukin-6 (IL-6) Therapy with Monoclonal Antibodies: Enhancement of IL-6 Clearance by Cocktails of Anti-IL-6 Antibodies", *Blood*; vol. 85; pp. 917-924; 1995.
N. Nishimoto et al; "Clinical Application of Interleukin-6 receptor antibody"; *Japanese Society for Immunology*; vol. 20 (2); pp. 87-94; 1997.
A. Ogata et al; "Advances in Interleukin-6 Therapy"; *Clinical Pathology*; vol. 47(4); pp. 321-326, 1999.
K. Sato et al; "Humanization of an anti-human IL-6 mouse monoclonal antibody glycosylated in its heavy chain variable region"; *Human Antibody Hybridomas*; vol. 7(4), pp. 175-193; 1996.
D. Wendling at al; "Treatment of Severe Rheumatoid Arthritis by anti-interleukin 6 monoclonal antibody"; "*Journal Rheumatology*"; vol. 20(2); pp. 259-262; 1993.
J. Wijdenes et al "Human Recombinant Dimeric IL-6 Binds to Its Receptor as Detected by Anti-IL-6 Monoclonal Antibodies"; *Molecular Immunology*; vol. 28(11), pp. 1183-1192; 1991.
G. Vreugdenhil et al; "Anaemia of chronic disease in rheumatoid arthritis"; *Rheumatol Int.*, vol. 10 (3), pp. 127-130; 1990.

* cited by examiner

*Primary Examiner*—Michail A. Belyavskyi
*Assistant Examiner*—Zachary Skelding
(74) *Attorney, Agent, or Firm*—Browdy and Neimark, P.L.L.C.

(57) ABSTRACT

A substance effective for treating immunopathy where interleukin 6 (IL-6) is involved is provided. A human anti-human IL-6 antibody and a human anti-human IL-6 antibody fragment having a high affinity to human IL-6 were obtained using phage antibody technique. The antibody and antibody fragment are expected to be useful as a medicament for treating inflammation and immunopathy caused by IL-6.

2 Claims, 3 Drawing Sheets

HUMAN ANTIHUMAN INTERLEUKIN-6 ANTIBODY AND FRAGMENT OF ANTIBODY

TECHNICAL FIELD

The present invention relates to a human anti-human interleukin-6 (hereinafter referred to as "IL-6") antibody that binds to human IL-6 to thereby block binding between IL-6 and its receptor, a fragment of said antibody, and a gene fragment encoding the same. The antibody and a fragment thereof according to the present invention are expected to be useful as a medicament for treating inflammation and immunopathy caused by IL-6.

BACKGROUND ART

IL-6 is a glycoprotein with a molecular weight of 21,000 that is produced from T cells, macrophages, fibroblasts, muscular cells and the like when stimulated with a mitogen, viral infection, or IL-1. Human IL-6 consists of 184 amino acids and its gene is present on the 7th chromosome. IL-6 has diverse biological activities including (1) induction of cellular proliferation (hybridomas, T cells, keratinocytes, renal mesangial cells), (2) inhibition of cellular proliferation (myelogenic leukemia cell lines, malignant melanoma cell lines), and (3) induction of cellular differentiation and induction of production of cellular specific proteins (neural differentiation of melanocytoma cell lines, differentiation of killer T cells, maturation of megakaryocytes, differentiation into macrophages of myelogenic leukemia cell lines, antibody production of B cells, production of acute phase proteins in hepatocytes). Due to its diverse biological activities, it has been indicated that IL-6 may be relevant to some diseases. In recent years, it is known that IL-6 is involved in onset of diseases including (1) rheumatoid arthritis, atrial myxoma, Castleman disease, hypergammaglobulinemia or autoimmune symptoms in AIDS, (2) mesangial nephritis, (3) psoriasis, and (4) Kaposi sarcoma in AIDS. Recently, it is also known that a large quantity of IL-6 is produced from the skeletal muscle immediately after physical practice, which stimulates hypothalamus to secrete various neurohormones to thereby affect the immune system (Dictionary of Immunology, 1st ed., p. 49, 1993).

Among the diseases where IL-6 is involved, rheumatoid arthritis (RA) afflicts about $7 \times 10^5$ people all over the country in Japan with gradual increase and together with increase in the number of aged patients is becoming a social problem (Ogata A. et al., Rinsho Byori (Clinical Pathology), 1999 April; 47 (4): 321-326 [Advances in interleukin-6 therapy]).

The cause of RA is not known. RA, an autoimmune disease wherein an autoimmune reaction within the articular cavity has continued and became chronic, is assigned as one of inveterate specific diseases. Relevancy of RA to IL-6 has been investigated to reveal that a large quantity of IL-6 is present in joint fluid from RA patients and that IL-6 is involved not only in induction of inflammation but also in proliferation of fibroblasts in the synovial membrane. There is also possibility that IL-6 may accelerate production of autoantibody (Nishimoto N. et al., Clinical application of interleukin-6 receptor antibody, transactions of Japanese Society for Immunology 1997; 20: 87-94).

Accordingly, anti-IL-6 antibody that inhibits the biological activities of IL-6 would be a candidate of a nosotropic medicament for treating several immunopathies including RA and is practically under investigation (Mihara M. et al., Br. J. Rheumatol. 1995 April; 34(4): 321-325; Mihara M. et al., Clin. Immunol. 2001, 98: 319-326).

DISCLOSURE OF THE INVENTION (Technical Problems to be Solved by the Invention)

For RA patients, a wide variety of treatments have been applied including drug therapy with non-steroidal antiinflammatory, analgesic agents, steroidal agents, immunosuppressive agents or antimetabolites, and surgical therapy such as artificial joint, depending on a disease stage of patients. However, these therapies are not eradicative for RA but there are problems of adverse side effects due to application of therapies for a long period of time with a large amount of drugs. IL-6 plays a role in enhancement of inflammation and hence is a major cause of pain RA patients suffered from. It has been indicated therefore that inhibition of the IL-6 activity would alleviate the pain. As a candidate, a humanized anti-IL-6 antibody has been investigated (Montero-Julian F. A. et al., Blood 1995 February 15; 85(4): 917-24; Monier S. et al, Clin. Exp. Rheumatol. 1994 November-December; 12(6): 595-602; Wendling D. et al, J. Rheumatol. 1993 February; 20(2): 259-62).

On the other hand, IL-6 has an activity of a growth factor to myeloma cells (Dictionary of Immunology, 1st ed., p. 49, 1993; aforementioned) and hence causes a problem that, even if hybridomas producing an antibody that binds to IL-6 with high affinity were obtained, their proliferation is hampered through neutralization of IL-6 in the culture medium by the produced antibody and as a result obtaining an anti-IL-6 antibody with high affinity has been difficult. Sato et al. reported that an anti-human IL-6 antibody obtained from mice exhibited high affinity of 11 nM but also with a high dissociation rate of $3 \times 10^{-2}$ sec. (Sato K. et al., Hum. Antibodies Hybridomas 1996; 7(4): 175-83). With such an antibody having a high dissociation rate as obtained by the prior art techniques, maintenance of a high concentration of the antibody was necessary for inhibiting the IL-6 activity. Much less, an antibody with such an activity is never known that is a wholly human antibody.

Besides, unlike a wholly human antibody, a possibility could not be denied that administration of a humanized antibody to patients would lead to production in patients of an antibody (blocking antibody) that inhibits the activity of the anti-IL-6 antibody.

(Means to Solve the Problems)

Under the circumstances, the present inventors devised a screening system with the phage antibody technique to thereby obtain a wholly human anti-human IL-6 antibody single chain Fv (scFv) molecule and elucidated VH and VL chains of said antibody. The present inventors further analyzed the properties of said scFv to reveal that said scFv exhibited a significantly lower association rate as compared to those of the conventional antibodies against human IL-6 obtained from a variety of animals (in the order of $10^{-3}$ sec; dissociation rate being about 40-folds lower than that of conventional ones), had an equivalent or higher affinity to IL-6 as compared to the conventional antibodies, and inhibited proliferation of IL-6 dependent cell lines in a concentration dependent manner.

(More Efficacious Effects than Prior Art)

It is expected that the use of such an antibody that is wholly derived from human and has a high affinity to IL-6 would exert therapeutic effects with a lower antibody concentration than a chimeric antibody or a humanized antibody to thereby produce only an extremely low level of anti-idiotype antibody against said antibody and hence would provide an anti-human IL-6 antibody drug that will exhibit excellent therapeutic effects as an anti-IL-6 antagonist for treating autoimmune diseases such as IL-6 dependent leukemia and rheumatoid arthritis. The antibody according to the present invention is also expected for use as a medicament for treating acute inflammation with reduced side effects and with potent activity.

BEST MODE FOR CARRYING OUT THE INVENTION

Figure 1:
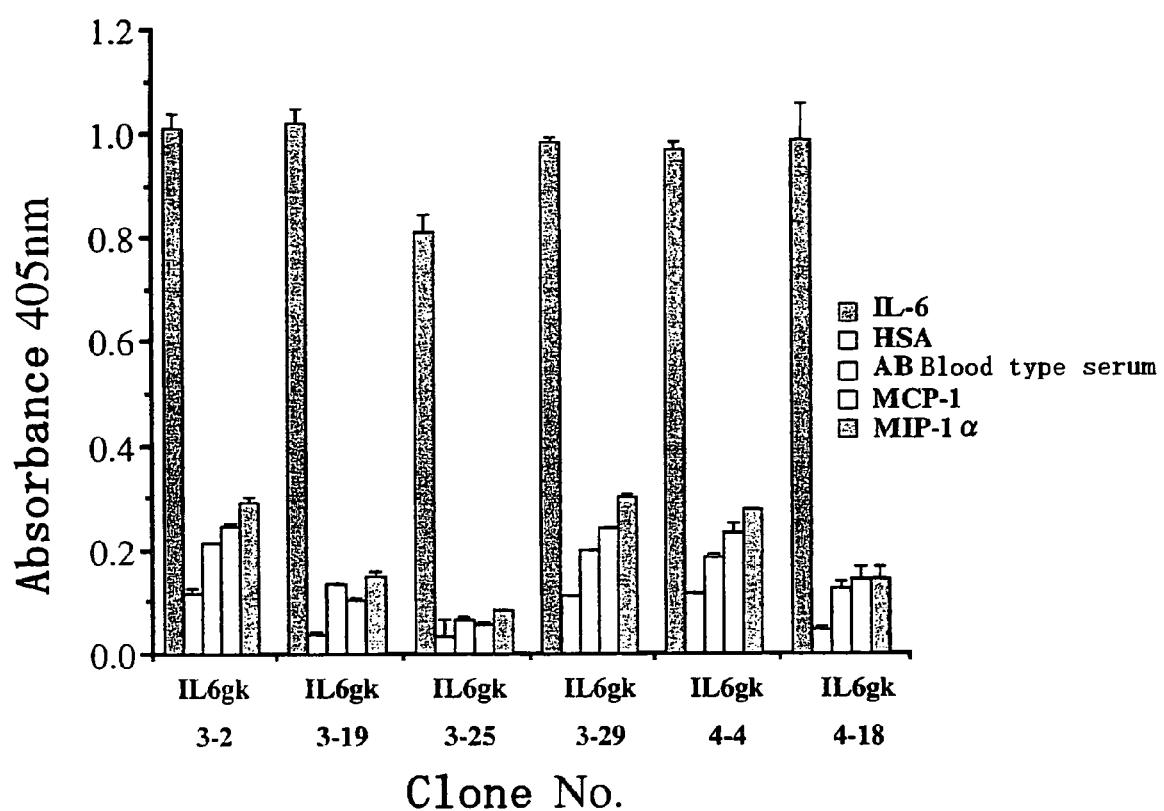
FIG. 1 is a graph showing the results of ELISA where reactivity of IL6gk3-2scFv from IL-6gk series with a recombinant IL-6, human serum albumin (HSA), AB blood type serum, monocyte chemoattractant protein-1 (MCP-1) and MIP-1α (macrophage inflammatory protein-1α) was measured.

From peripheral B lymphocytes taken from 20 healthy donors, cDNAs of each of immunoglobulin heavy (H) chain and light (L) chain were amplified by RT-PCR and combined together with a linker DNA to prepare single chain Fv (scFv) DNAs where the VH chain and VL chain DNAs from lymphocytes of healthy donors were in random combination.

The scFv DNAs were incorporated into phagemid vector pCANTAB5E to prepare a scFv display phage library consisting of $10^9$ clones from healthy donors. This library was then combined with a human IL-6 immobilized on a solid phase and an anti-human IL-6 Fv display phage clone was recovered, concentrated and screened. As a result, the screened scFv clone (IL6gk3-2) produced scFv antibody that binds to a human IL-6.

The scFv antibody produced by the clone IL6gk3-2, in spite of being a single chain, specifically bound to a ligand (IL-6) with an affinity equivalent to the usual complete antibody.

The scFv antibody produced by the clone IL6gk3-2, when added to KT-3 cell line that proliferates in a human IL-6 dependent manner, inhibited IL-6 dependent proliferation response of said cell line in a concentration dependent manner.

The amino acid sequences of VH and VL chains of the above scFv clone having the inhibitory activity as well as the nucleotide sequences coding therefor are indicated in SEQ ID NOs: 1 and 2 (VH chain) and in SEQ ID NOs: 3 and 4 (VL chain), respectively.

In addition, the amino acid sequences of complementarity determining regions (CDR1 to CDR3), which are included in the above amino acid sequences, of VH and VL chains are shown below.

```
[VH chain]
CDR1:
Lys Tyr Tyr Met Ala         (SEQ ID NO: 5)

CDR2:
Thr Ile Ser Asn Ser Gly Asp Ile   (SEQ ID NO: 6)
Ile Asp Tyr Ala Asp Ser Val Arg
Gly
```

```
-continued
CDR3:
Glu Tyr Phe Phe Ser Phe Asp Val   (SEQ ID NO: 7)

[VL chain]
CDR1:
Arg Ala Ser Gln Asp Ile Arg Asn   (SEQ ID NO: 8)
Trp Val Ala

CDR2:
Asp Gly Ser Ser Leu Gln Ser       (SEQ ID NO: 9)

CDR3:
Gln Gln Ser Asp Ser Thr Pro Ile   (SEQ ID NO: 10)
Thr Phe
```

An antibody fragment having a variable region of either the VH chain or the VL chain as described above or variable regions of both VH and VL chains has a variable region of a human anti-human IL-6 antibody and strongly interacts with human IL-6 to thereby exert an inhibitory activity against the binding between IL-6 and an IL-6 receptor.

Although the VH chain and/or the VL chain of the human anti-human IL-6 antibody as disclosed herein were obtained in the form of scFv by the phage antibody technique, the present invention encompasses a human anti-human IL-6 antibody in the form of a complete molecule wherein the disclosed VH chain and/or VL chain are bound to a constant region of a human immunoglobulin, a human anti-human IL-6 antibody fragment such as Fab, Fab' or F(ab')$_2$ wherein the disclosed VH chain and/or VL chain are combined with a portion of a constant region of a human immunoglobulin, and other human anti-human IL-6 antibody fragment such as a human anti-human IL-6 single chain antibody (scAb) wherein scFv is bound to a constant region of a human immunoglobulin, as well as gene fragments encoding these antibodies and the antibody fragments. The present invention further encompasses a modified protein molecule wherein a high molecular weight modifying agent is bound to these antibody and antibody fragment protein molecules.

INDUSTRIAL APPLICABILITY

As described above, the human anti-human IL-6 antibody and the fragment molecules of said antibody according to the present invention may inhibit various immune responses induced by binding between IL-6 and an IL-6 receptor and hence may be used as an anti-inflammatory, analgesic agent or as a medicament for the treatment and prevention of autoimmune diseases.

Besides, the human anti-human IL-6 antibody and the fragment molecules of said antibody according to the present invention, in view of their property, may provide an immunological measurement for detection or measurement of IL-6 expressing cells in human peripheral blood or in muscles.

In addition, the human anti-human IL-6 antibody and the fragment molecules of said antibody according to the present invention may further provide many other applications when complexed with an immunoadsorbent consisting of an immunologically inactive adsorbent. For instance, IL-6 present in human peripheral blood may be purified with immunoaffinity chromatography. Such an immunoadsorbent complex may also be used for purification of IL-6 in a culture supernatant produced by culture cells transformed by the genetic recombination.

Besides, peptides of the variable region of the human anti-human IL-6 antibody of the present invention and derivatives of said peptides may provide a new means for isolating a peptide or an anti-idiotype antibody that recognizes the human anti-human IL-6 antibody of the present invention from a library. The obtained peptides and the anti-idiotype antibodies and derivatives thereof are expected to be efficacious for treating acute inflammation due to IL-6 neutralization or autoimmune diseases (Vreugdenhil G. et al., *Rheumatol. Int.* 1990; 10(3): 127-30; Hirano T. et al., *Ric. Clin. Lab.* 1989 January-March; 19(1): 1-10).

The present invention is explained in more detail by means of the following Examples but should not be construed to be limited thereto.

EXAMPLE 1

Construction of Phage Library from Healthy Donors

Phage library was constructed as reported by J. D. Marks et al., *J. Mol. Biol.*, 222: 581-597, 1991 with some modification.

Lymphocytes were isolated from peripheral blood taken from 20 healthy donors by sedimentary centrifugation with Ficol, washed thoroughly with PBS and then treated with ISOGEN (NIPPON GENE CO., LTD) to prepare a total RNA. The obtained total RNA was divided into four samples and from each of the samples were prepared cDNAs with primers specific to constant regions of either human IgG, IgM, κ chain or λ chain using first strand cDNA synthesis kit (Pharmacia biotech). Using each of the obtained cDNAs as a template, each of antibody V region genes were amplified by polymerase chain reaction (PCR) using primers specific to either of combinations of VH(γ or µ) and JH, Vκ and Jκ, or Vλ and Jλ, as described by Marks et al.

Then, VH (γ or µ) and Vκ, and VH (γ or µ) and Vλ, were linked together with a linker DNA by assembly PCR (McCafferty, J. et al.: Antibody Engineering—A Practical Approach, IRL Press, Oxford, 1996) to prepare single chain scFv DNAs. The obtained scFv DNAs were added with NotI and SfiI restriction sites using PCR, electrophoresed on agarose gel and then purified. The purified scFv DNAs were digested with the restriction enzymes NotI (Takara) and SfiI (Takara) and then cloned into phagemid pCANTAB5E (Pharmacia). The obtained phagemids pCANTAB5E where scFv DNA was bound were introduced into *E. coli* TG1 cells by electroporation for each of VH(γ)-Vκ, VH(γ)-Vλ, VH(µ)-Vκ, and VH(µ)-Vλ. From the number of the transformed TG1 cells, it was assessed that VH(γ)-Vκ, VH(γ)-Vλ, VH(µ)-Vκ and VH(µ)-Vλ exhibited diversity of $1.1 \times 10^8$, $2.1 \times 10^8$, $8.4 \times 10^7$ and $5.3 \times 10^7$ clones, respectively. With M13KO7 helper phage, phage antibodies were expressed on the transformed TG1 cells to prepare scFv display phage library derived from healthy donors.

EXAMPLE 2

Panning

Human IL-6 was dissolved in 1 mL $0.1M$ $NaHCO_3$ and the solution was incubated in 35 mm dish (Iwaki) at 4° C. overnight to immobilize IL-6. To the dish was added 0.5% gelatin/PBS for blocking at 20° C. for 2 hours and then the dish was washed six times with 0.1% Tween20-PBS. To the dish was then added 0.9 mL of the single chain antibody display phage solution ($1 \times 10^{12}$ tu/mL of the antibody phage library derived from healthy donors) for reaction.

After washing the dish ten times with 0.1% Tween20-PBS, 1.0 mL glycine buffer (pH 2.2) was added to elute single chain antibody display phages bound to IL-6. After adjusting pH by adding 1M Tris (hydroxymethyl)-aminomethane-HCl, pH9.1, the eluted phages were infected to *E. coli* TG1 cells at logarithmic growth phase. The infected TG1 cells were centrifuged at 3,000×g for 10 minutes. Supernatant was removed, suspended in 200 µL 2×YT culture medium, plated on SOBAG plate (SOB plate containing 2% glucose, 100 µg/ml ampicillin) and then incubated overnight in an incubator at 30° C. The resulting colonies were suspended and recovered in a suitable amount of 2×YT culture medium with a scraper (Coastor).

The obtained TG1 solution (50 µL) was inoculated on 30 mL 2×YT culture medium and rescued with a helper phage to prepare a phage library after screening.

For each of the phage libraries VH(γ)-Vκ, VH(γ)-Vλ, VH(µ)-Vκ and VH(µ)-Vλ derived from healthy donors, four pannings in total were performed with the IL-6 immobilized plate. After the fourth panning, any clone was extracted arbitrarily from the SOBAG plate. The scFv expression was confirmed, specificity was confirmed by IL-6 ELISA and a nucleotide sequence was analyzed.

EXAMPLE 3

IL-6 ELISA for Screening

For screening the isolated clones, ELISA was performed as follows: Human IL-6 and control proteins were immobilized on an ELISA plate for screening. Each 40 µL/well of a human recombinant IL-6 (1.25 µg/mL), a human serum albumin (HSA; 2.5 µg/mL), a human monocyte chemoattractant protein 1 (MCP-1; 1.25 µg/mL), a human MIP-1α (macrophage inflammatory protein 1-α; 1.25 µg/mL) or a human AB blood type serum (1.25 µg/mL) were placed in an ELISA plate (Nunc) which was kept standing at 4° C. for 16 hours for immobilization. The immobilized plate was added with 400 µL/well of a PBS solution containing 0.5% BSA, 0.5% gelatin and 5% skimmed milk and was kept standing at 4° C. for 2 hours for blocking.

To the plate was added 40 µL/well of sample solutions containing scFv display phage for reaction. The sample solutions were discarded and the plate was washed with a washing solution five times. The plate was reacted with biotin-labeled anti-M13 monoclonal antibody (Pharmacia biotech) and then with anti-mouse IgG antibody labeled with alkaline phosphatase (AP). After washing with a washing solution five times, the plate was added with 50 µL/well of a developing solution of substrate, i.e. a PBS solution containing 1 g/mL p-nitrophenyl phosphate (Wako) and 10% diethanolamine (Wako), light-shielded, and developed at room temperature to 37° C. for 5 to 10 minutes. Absorbance at 405 nm was measured using Multiplate Autoreader NJ-2001 (Inter Med). As a result, all the clones assessed were confirmed to be specific to IL-6 (FIG. 1).

EXAMPLE 4

Sequence Analysis of Clones

A DNA nucleotide sequence of the isolated clones was determined for scFv gene VH and VL using Dye terminator cycle sequencing FS Ready Reaction kit (Applied Biosystems) As a result of ELISA and sequence analysis, the isolated clones were classified into four classes. Among these, the clone IL6gk3-2 had nucleotide sequences of VH and VL as shown in SEQ ID NOs: 1 and 3, respectively.

EXAMPLE 5

Expression and Recovery of scFv

A soluble scFv was expressed with *E. coli* HB2151, recovered from *E. coli* periplasm fraction and crudely purified. If further purification was necessary, affinity purification was performed with RAPAS Purification Module (Pharmacia Biotech). Purity of the purified scFv protein was confirmed by SDS-polyacrylamide gel electrophoresis and Western blotting where Etag epitope at the C-terminus of the scFv protein was targeted. For determination of a protein concentration of the purified scFv protein product, Protein Assay Kit (BIO-RAD) was used.

EXAMPLE 6

Affinity Measurement of Purified scFv by SPR

Figure 2:
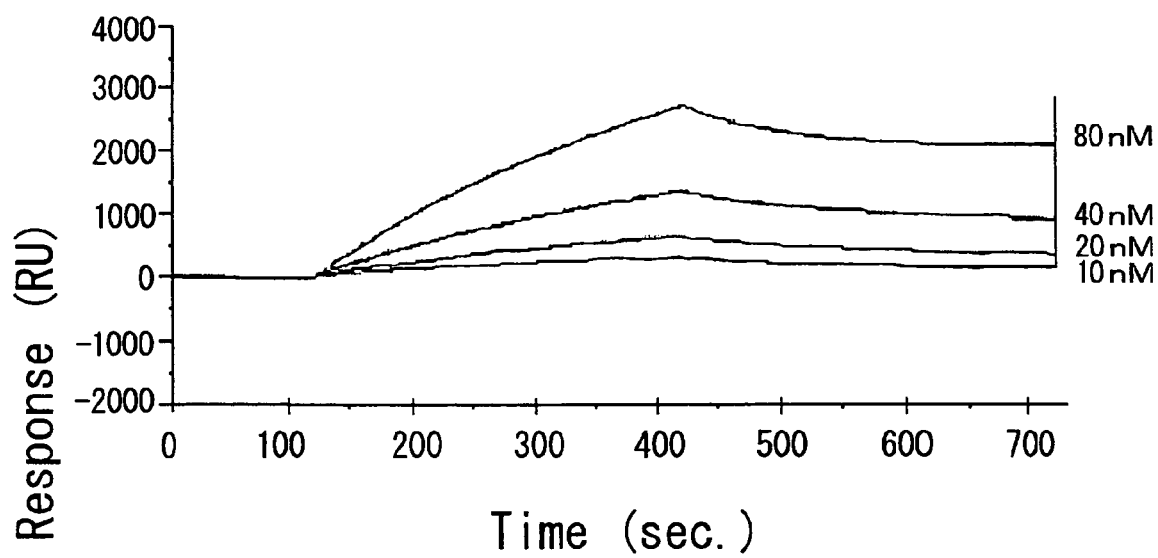
FIG. 2 is a graph showing the results of BIA CORE where a binding affinity of IL6gk3-2 scFv with IL-6 was measured.

Using BIAcore (BIAcore), affinity of the purified scFv was measured by SPR. As a result, IL6gk3-2, the clone with the highest affinity among the isolated clones, was assessed to have $13 \times 10^{-9}$ M of a dissociation constant (FIG. 2).

EXAMPLE 7

Effect on Proliferation Response of IL-6 Dependent Cell Line

Figure 3:
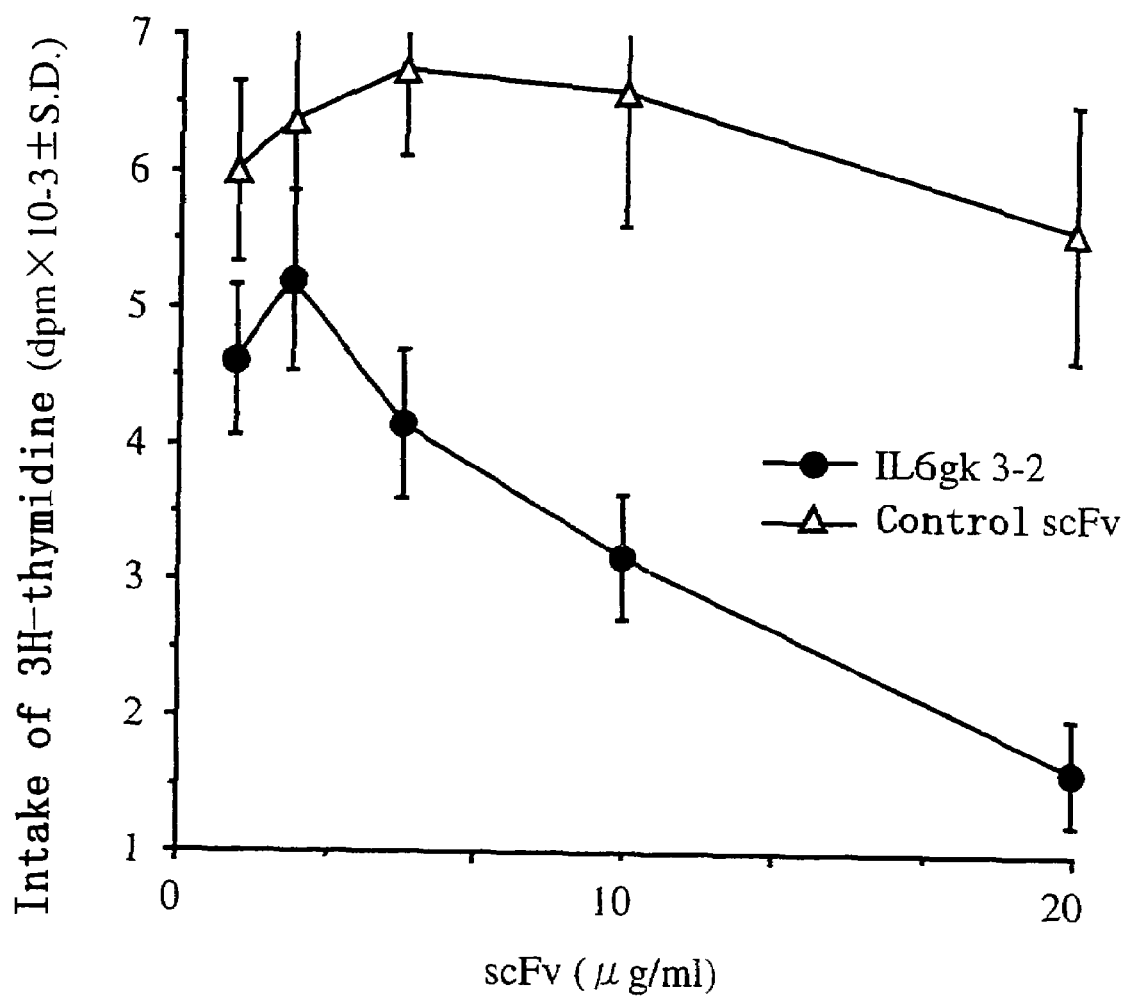
FIG. 3 is a graph showing the results that IL6gk3-2 scFv inhibited IL-6 dependent proliferation response of IL-6 dependent cell line KT-3.

The purified scFv was assessed for its inhibitory activity on IL-6 dependent proliferation response of cell line KT-3 that proliferates in an IL-6 dependent manner. KT-3 cells prepared at $2 \times 10^4$ cells/200 μl/well were cultured for four days in the presence of 1.25 to 20 μg/ml of the purified scFv from the clone IL6gk3-2 and IL-6 (80 pg/ml) and were assessed for DNA synthesis through thymidine intake. As a result, it was revealed that the scFv from the clone IL6gk3-2 inhibited proliferation response of KT-3 cells in a concentration dependent manner (FIG. 3).

The invention claimed is:

1. A gene fragment coding for a single chain Fv (hereinafter referred to as "scFv") of a human anti-human IL-6 antibody that binds to human IL-6 with a dissociation constant ($K_D$) of $1.0 \times 10^{-8}$ M or less, said gene fragment consisting of a gene fragment coding for a VH chain of said human anti-human IL-6 antibody bound to a gene fragment coding for a VL chain of said human anti-human IL-6 antibody;

wherein complementarity determining regions (CDR1 to CDR3) of said VH chain have the following amino acid sequences:

```
CDR1:
Lys Tyr Tyr Met Ala            (SEQ ID NO: 5)

CDR2:
Thr Ile Ser Asn Ser Gly Asp Ile Ile    (SEQ ID NO: 6)
Asp Tyr Ala Asp Ser Val Arg Gly

CDR3:
Glu Tyr Phe Phe Ser Phe Asp Val    (SEQ ID NO: 7)
``` and/or complementarity determining regions (CDR1 to CDR3) of said VL chain have the following amino acid sequences:

```
CDR1:
Arg Ala Ser Gln Asp Ile Arg Asn    (SEQ ID NO: 8)
Trp Val Ala

CDR2:
Asp Gly Ser Ser Leu Gln Ser        (SEQ ID NO: 9)

CDR3:
Gln Gln Ser Asp Ser Thr Pro Ile    (SEQ ID NO: 10)
Thr Phe.
```

2. A gene fragment coding for a single chain Fv (hereinafter referred to as "scFv") of a human anti-human IL-6 antibody that binds to human IL-6 with a dissactation constant ($K_D$) of $1.0 \times 10^{-8}$ M or less, said gene fragment consisting of a gene fragment coding for a VH chain of said human anti-human IL-6 antibody bound to a gene fragment coding for a VL chain of said human anti-human IL-6 antibody, wherein said VH chain has the amino acid sequence depicted in SEQ ID NO: 2 and/or said VL chain has the amino acid sequence depicted in SEQ ID NO: 4.

* * * * *

UNITED STATES PATENT AND TRADEMARK OFFICE
CERTIFICATE OF CORRECTION

| | | |
|---|---|---|
| PATENT NO. | : 7,482,436 B2 | Page 1 of 1 |
| APPLICATION NO. | : 10/526072 | |
| DATED | : January 27, 2009 | |
| INVENTOR(S) | : Sugimura et al. | |

It is certified that error appears in the above-identified patent and that said Letters Patent is hereby corrected as shown below:

On the title page,

[*] Notice:     Subject to any disclaimer, the term of this patent is extended or adjusted under 35 USC 154(b) by 427 days Delete the phrase "by 427 days" and insert -- by 761 days --

Signed and Sealed this

Twentieth Day of April, 2010

David J. Kappos
*Director of the United States Patent and Trademark Office*

```
                        SEQUENCE LISTING

<160> NUMBER OF SEQ ID NOS: 10

<210> SEQ ID NO 1
<211> LENGTH: 351
<212> TYPE: DNA
<213> ORGANISM: Homo sapiens

<400> SEQUENCE: 1 cag gtc aac tta agg gag tct ggg gga gac ttg gtc aag ccc gga ggg        48
Gln Val Asn Leu Arg Glu Ser Gly Gly Asp Leu Val Lys Pro Gly Gly
                5                   10                  15 tcc cta aga ctc tca tgt gca gcc tct gga ttc acc ttc aga aag tat        96
Ser Leu Arg Leu Ser Cys Ala Ala Ser Gly Phe Thr Phe Arg Lys Tyr
            20                  25                  30 tac atg gcc tgg atc cgc cag gct cca ggg aag ggg ccg gag tgg ctt       144
Tyr Met Ala Trp Ile Arg Gln Ala Pro Gly Lys Gly Pro Glu Trp Leu
        35                  40                  45 tca acc att agt aac agc ggt gat atc ata gac tat gca gac tct gtg       192
Ser Thr Ile Ser Asn Ser Gly Asp Ile Ile Asp Tyr Ala Asp Ser Val
    50                  55                  60 agg ggc cgg ttc tcc atc tcc agg gac aat gcc cag aag tca ctg tat       240
Arg Gly Arg Phe Ser Ile Ser Arg Asp Asn Ala Gln Lys Ser Leu Tyr
65                  70                  75                  80 ctg caa atg acc tcc ctg aga ccc gac gac tcg gcc atc tat tac tgt       288
Leu Gln Met Thr Ser Leu Arg Pro Asp Asp Ser Ala Ile Tyr Tyr Cys
                85                  90                  95 gcg agg gaa tat ttc ttt tct ttt gat gtg tgg ggc cga ggg aca atg       336
Ala Arg Glu Tyr Phe Phe Ser Phe Asp Val Trp Gly Arg Gly Thr Met
            100                 105                 110 gtc acc gtc tcc tca                                                   351
Val Thr Val Ser Ser
        115

<210> SEQ ID NO 2
<211> LENGTH: 117
<212> TYPE: PRT
<213> ORGANISM: Homo sapiens

<400> SEQUENCE: 2

Gln Val Asn Leu Arg Glu Ser Gly Gly Asp Leu Val Lys Pro Gly Gly
                5                   10                  15

Ser Leu Arg Leu Ser Cys Ala Ala Ser Gly Phe Thr Phe Arg Lys Tyr
            20                  25                  30
```

```
Tyr Met Ala Trp Ile Arg Gln Ala Pro Gly Lys Gly Pro Glu Trp Leu
            35                  40                  45

Ser Thr Ile Ser Asn Ser Gly Asp Ile Ile Asp Tyr Ala Asp Ser Val
 50                  55                  60

Arg Gly Arg Phe Ser Ile Ser Arg Asp Asn Ala Gln Lys Ser Leu Tyr
 65                  70                  75                  80

Leu Gln Met Thr Ser Leu Arg Pro Asp Asp Ser Ala Ile Tyr Tyr Cys
                 85                  90                  95

Ala Arg Glu Tyr Phe Phe Ser Phe Asp Val Trp Gly Arg Gly Thr Met
                100                 105                 110

Val Thr Val Ser Ser
            115

<210> SEQ ID NO 3
<211> LENGTH: 324
<212> TYPE: DNA
<213> ORGANISM: Homo sapiens

<400> SEQUENCE: 3 gac atc gtg atg acc cag tct cca tct tct gtg tct gca tcg gtg gga      48
Asp Ile Val Met Thr Gln Ser Pro Ser Ser Val Ser Ala Ser Val Gly
 1               5                  10                  15 gac aga gtc acc atc ttt tgt cgg gcg agt cag gat att agg aat tgg      96
Asp Arg Val Thr Ile Phe Cys Arg Ala Ser Gln Asp Ile Arg Asn Trp
             20                  25                  30 gta gcc tgg tat caa cag aaa cca ggt gag gcc cct aaa tta ttg atc     144
Val Ala Trp Tyr Gln Gln Lys Pro Gly Glu Ala Pro Lys Leu Leu Ile
         35                  40                  45 tat gat gga tcg agt ttg caa agt ggg gtc cca tca agg ttc agc ggc     192
Tyr Asp Gly Ser Ser Leu Gln Ser Gly Val Pro Ser Arg Phe Ser Gly
     50                  55                  60 agt gga tct ggg aca gaa ttc act ctc aca atc agc agc ctg cag cct     240
Ser Gly Ser Gly Thr Glu Phe Thr Leu Thr Ile Ser Ser Leu Gln Pro
 65                  70                  75                  80 gaa gat ttt gca act tac tac tgt caa cag agt gac agt acc cct att     288
Glu Asp Phe Ala Thr Tyr Tyr Cys Gln Gln Ser Asp Ser Thr Pro Ile
                 85                  90                  95 acc ttc ggc caa ggg aca cga ctg gag att aaa cgt                     324
Thr Phe Gly Gln Gly Thr Arg Leu Glu Ile Lys Arg
                100                 105

<210> SEQ ID NO 4
<211> LENGTH: 108
<212> TYPE: PRT
<213> ORGANISM: Homo sapiens

<400> SEQUENCE: 4

Asp Ile Val Met Thr Gln Ser Pro Ser Ser Val Ser Ala Ser Val Gly
 1               5                  10                  15

Asp Arg Val Thr Ile Phe Cys Arg Ala Ser Gln Asp Ile Arg Asn Trp
             20                  25                  30

Val Ala Trp Tyr Gln Gln Lys Pro Gly Glu Ala Pro Lys Leu Leu Ile
         35                  40                  45

Tyr Asp Gly Ser Ser Leu Gln Ser Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Ser Asp Ser Thr Pro Ile
```

```
                    85                  90                  95
Thr Phe Gly Gln Gly Thr Arg Leu Glu Ile Lys Arg
            100                 105

<210> SEQ ID NO 5
<211> LENGTH: 5
<212> TYPE: PRT
<213> ORGANISM: Homo sapiens
<220> FEATURE:
<223> OTHER INFORMATION: CDR1 corresponding to amino acids No. 31 to No.
      35 in SEQ ID NO: 2

<400> SEQUENCE: 5

Lys Tyr Tyr Met Ala
1               5

<210> SEQ ID NO 6
<211> LENGTH: 17
<212> TYPE: PRT
<213> ORGANISM: Homo sapiens
<220> FEATURE:
<223> OTHER INFORMATION: CDR2 corresponding to amino acids No. 50 to No.
      66 in SEQ ID NO: 2

<400> SEQUENCE: 6

Thr Ile Ser Asn Ser Gly Asp Ile Ile Asp Tyr Ala Asp Ser Val Arg Gly
1               5                   10                  15

<210> SEQ ID NO 7
<211> LENGTH: 8
<212> TYPE: PRT
<213> ORGANISM: Homo sapiens
<220> FEATURE:
<223> OTHER INFORMATION: CDR3 corresponding to amino acids No. 99 to No.
      106 in SEQ ID NO: 2

<400> SEQUENCE: 7

Glu Tyr Phe Phe Ser Phe Asp Val
1               5

<210> SEQ ID NO 8
<211> LENGTH: 11
<212> TYPE: PRT
<213> ORGANISM: Homo sapiens
<220> FEATURE:
<223> OTHER INFORMATION: CDR1 of corresponding to amino acids No. 24 to
      No. 34 in SEQ ID NO: 4

<400> SEQUENCE: 8

Arg Ala Ser Gln Asp Ile Arg Asn Trp Val Ala
1               5                   10

<210> SEQ ID NO 9
<211> LENGTH: 7
<212> TYPE: PRT
<213> ORGANISM: Homo sapiens
<220> FEATURE:
<223> OTHER INFORMATION: CDR2 corresponding to amino acids No. 50 to No.
      56 in SEQ ID NO: 4

<400> SEQUENCE: 9

Asp Gly Ser Ser Leu Gln Ser
1               5

<210> SEQ ID NO 10
<211> LENGTH: 10
<212> TYPE: PRT
```

```
<213> ORGANISM: Homo sapiens
<220> FEATURE:
<223> OTHER INFORMATION: CDR3 corresponding to amino acids No. 89 to No.
      98 in SEQ ID NO: 4

<400> SEQUENCE: 10

Gln Gln Ser Asp Ser Thr Pro Ile Thr Phe
1               5                   10
```